United States Patent
Chaligne (10) Patent No.: US 11,623,192 B2
(45) Date of Patent: Apr. 11, 2023

(54) AUTONOMOUS VACUUM PUMP

(71) Applicant: ZIMMER GMBH, Winterthur (CH)

(72) Inventor: Sebastien Chaligne, Brette les Pins (FR)

(73) Assignee: Zimmer GmbH, Winterthur (CH)

( * ) Notice: Subject to any disclaimer, the term of this patent is extended or adjusted under 35 U.S.C. 154(b) by 881 days.

(21) Appl. No.: 16/538,243

(22) Filed: Aug. 12, 2019

(65) Prior Publication Data

US 2020/0061558 A1 Feb. 27, 2020

Related U.S. Application Data

(60) Provisional application No. 62/720,476, filed on Aug. 21, 2018.

(51) Int. Cl.
| | |
|---|---|
| *B01F 33/70* | (2022.01) |
| *F04D 29/12* | (2006.01) |
| *F04F 5/48* | (2006.01) |
| *A61B 17/88* | (2006.01) |
| *B01F 31/40* | (2022.01) |
| *B01F 101/20* | (2022.01) |

(52) U.S. Cl.
CPC .............. *B01F 33/70* (2022.01); *F04D 29/12* (2013.01); *F04F 5/48* (2013.01); *A61B 2017/8838* (2013.01); *B01F 31/40* (2022.01); *B01F 2101/20* (2022.01)

(58) Field of Classification Search
CPC ......... B01F 2012/20; A61B 2017/8838; F04D 29/12; F04F 5/48
USPC .......................................................... 366/2
See application file for complete search history.

(56) References Cited

U.S. PATENT DOCUMENTS

| | | |
|---|---|---|
| 4,758,096 A | 7/1988 | Gunnarsson |
| 5,788,463 A * | 8/1998 | Chan .................. F04B 39/0016 |
| | | 417/63 |
| 5,797,680 A | 8/1998 | Murray |
| 5,934,803 A | 8/1999 | Hutter |
| 9,724,661 B2 | 8/2017 | Giffard et al. |
| 9,861,943 B2 | 1/2018 | Vogt et al. |

(Continued)

FOREIGN PATENT DOCUMENTS

| | | |
|---|---|---|
| EP | 1020167 A2 | 7/2000 |
| WO | WO-2018060494 A1 | 4/2018 |

OTHER PUBLICATIONS

"European Application Serial No. 19192935.5, Extended European Search Report dated Feb. 13, 2020", 6 pgs.

(Continued)

*Primary Examiner* — Marc C Howell
(74) *Attorney, Agent, or Firm* — Schwegman Lundberg & Woessner, P.A.

(57) ABSTRACT

An apparatus includes a pump body, two or more arms extending from the pump body configured to hold a cement mixing container, a vacuum port exposed on an exterior surface of the pump body and positioned to engage a port on the cement mixing container, a venturi positioned proximate the vacuum port; a perforator within the pump body, the perforator configured to puncture a gas container to release gas to the venturi to create a vacuum at the vacuum port; and an actuator configured to puncture the gas container with the perforator.

20 Claims, 6 Drawing Sheets

(56) References Cited

U.S. PATENT DOCUMENTS

2005/0130516 A1* 6/2005 Courtney ................. B63C 9/24
                                                     441/92
2013/0267864 A1   10/2013 Addington et al.
2016/0101246 A1    4/2016 Dennis et al.
2018/0326381 A1* 11/2018 Bradley ............... B01F 35/718

OTHER PUBLICATIONS

"European Application Serial No. 19192935.5, Response filed Sep. 17, 2020 to Extended European Search Report dated Feb. 13, 2020", 10 pgs.

* cited by examiner

AUTONOMOUS VACUUM PUMP

CLAIM OF PRIORITY

This application claims the benefit of U.S. Provisional Patent Application Ser. No. 62/720,476, filed on Aug. 21, 2018, the benefit of priority of which is claimed hereby, and which is incorporated by reference herein in its entirety.

FIELD

The present subject matter relates generally to orthopedic surgical devices, and more specifically to vacuum pump for mixing bone cement.

BACKGROUND

Bone cement can be prepared by mixing two or more substances. Before the cement hardens, the mixture has a soft composition which can be placed in the bone where a prosthesis is to be inserted.

While mixing the substances, considerable volumes of air can be incorporated within the mixture, and the more air the mixture contains, the more the solidity of the finished product deteriorates. To increase the solidity of the finished product, mixing of the substances is carried out in vacuum, whereby the supply of air to the mixture is minimized.

OVERVIEW

Example 1 can include subject matter that can include an apparatus including a pump body; two or more arms extending from the pump body configured to hold a cement mixing container; a vacuum port exposed on an exterior surface of the pump body and positioned to engage a port on the cement mixing container; a venturi positioned proximate the vacuum port; a perforator within the pump body, the perforator configured to puncture a gas container to release gas to the venturi to create a vacuum at the vacuum port; and an actuator configured to puncture the gas container with the perforator.

In Example 2, the subject matter of Example 1 can optionally include the two or more arms being curved so as to grip the sides of the cement mixing container.

In Example 3, the subject matter of any of Examples 1-2 can optionally include the vacuum port directly engaging the port on the cement mixing container without intervening hoses.

In Example 4, the subject matter of any of Examples 1-3 can optionally include the perforator including a body having a cavity on one end to receive a neck of the gas container.

In Example 5, the subject matter of Example 4 can optionally include the perforator including a needle located with the cavity to puncture the gas container, the perforator further including an arm extending from the body and having a passage so as to release gas out of a hole proximate the top of the arm.

In Example 6, the subject matter of Example 5 can optionally include a regulator inserted with the cavity of the perforator.

In Example 7, the subject matter of any of Examples 1-6 can optionally include the actuator including a lever rotatably coupled to the pump body.

In Example 8, the subject matter of Example 7 can optionally include the lever including a cam positioned such that when the lever is rotated the cam engages a bottom of the gas container and pushes the gas container up to the perforator.

In Example 9, the subject matter of any of Examples 1-8 can optionally include a seal member to receive a neck of the gas container, the seal member including an external O-ring to seal against an inner wall of a cavity of the perforator.

Example 10 can include subject matter that can include a system including a cement mixing container; a pump body; a gas container located within the pump body; two or more arms extending from the pump body configured to hold the cement mixing container; a vacuum port exposed on an exterior surface of the pump body and positioned to engage a port on the cement mixing container; a venturi positioned proximate the vacuum port; a perforator within the pump body, the perforator configured to puncture the gas container to release gas to the venturi to create a vacuum at the vacuum port; and an actuator configured to puncture the gas container with the perforator.

In Example 11, the subject matter of Example 10 can optionally include the vacuum port directly engaging the port on the cement mixing container without intervening hoses.

In Example 12, the subject matter of any of Examples 10-11 can optionally include the perforator including a body having a cavity on one end to receive a neck of the gas container.

In Example 13, the subject matter of Example 12 can optionally include the perforator including a needle located with the cavity to puncture the gas container, the perforator further including an arm extending from the body and having a passage so as to release gas out of a hole proximate the top of the arm.

In Example 14, the subject matter of Example 13 can optionally include a regulator inserted with the cavity of the perforator.

In Example 15, the subject matter of any of Examples 10-14 can optionally include the actuator including a lever rotatably coupled to the pump body.

In Example 16, the subject matter of Example 15 can optionally include the lever including a cam positioned such that when the lever is rotated the cam engages a bottom of the gas container and pushes the gas container up to the perforator.

In Example 17, the subject matter of any of Examples 10-16 can optionally include a seal member to receive a neck of the gas container, the seal member including an external O-ring to seal against an inner wall of a cavity of the perforator.

Example 18 can include subject matter that can include a method including attaching a vacuum pump directly to a cement mixing container such that a port on the cement mixing container directly engages a vacuum port on the vacuum pump; actuating the vacuum pump; and mixing a cement mixture with the cement mixing container.

In Example 19, the subject matter of Examples 18 can optionally include the vacuum pump including a gas container and a venturi.

In Example 20, the subject matter of Example 19 can optionally include a perforator within a pump body of the vacuum pump, the perforator configured to puncture the gas container to release gas to the venturi to create a vacuum at the vacuum port; and an actuator configured to puncture the gas container with the perforator.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
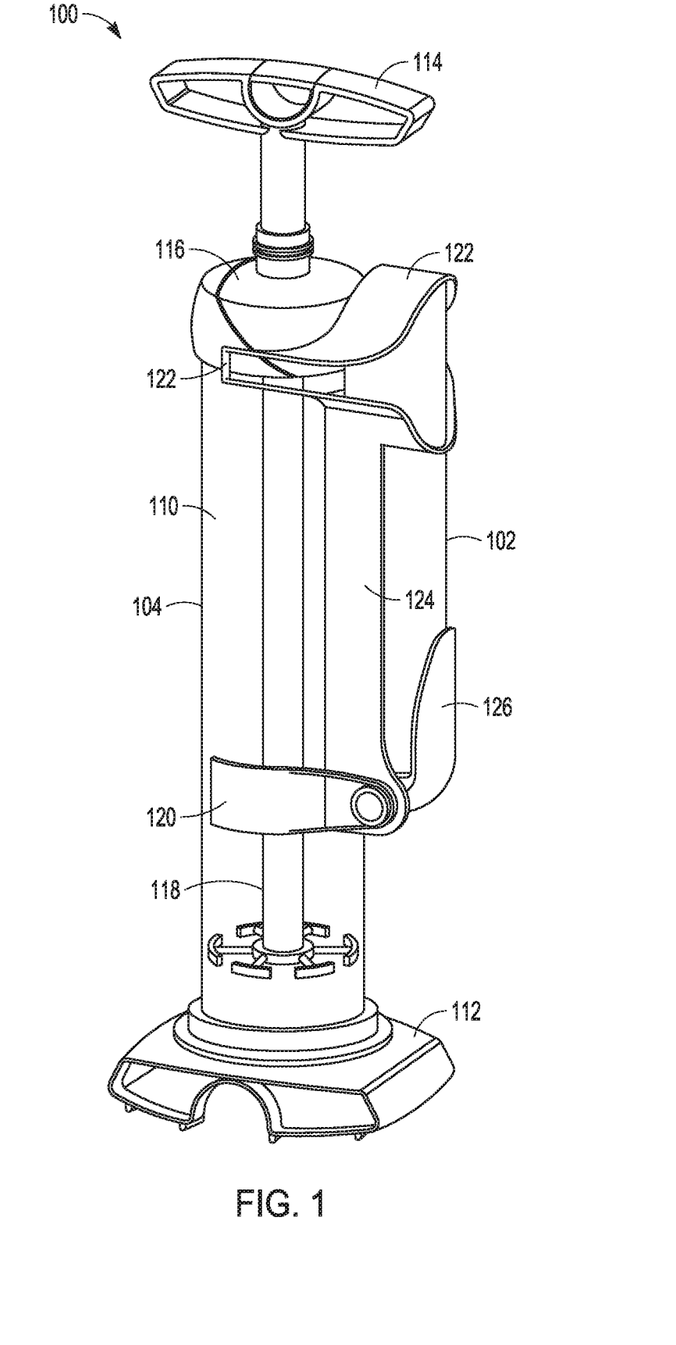
FIG. 1 shows an isometric view of a cement mixing system, in accordance with one embodiment.

FIG. 1 shows an isometric view of a cement mixing system 100, in accordance with one embodiment. System 100 includes a cement mixing container 104 and a vacuum pump 102 including a pump body 124. The vacuum pump 102 can be coupled to the cement mixing container by using two or more arms 120, 122.

The cement mixing container 104 includes a mixing cartridge 110 and a stand 112, a threaded cap 116, and a handle 114 which activates a mixing plate 118, In use, the cement materials to be mixed are put into the mixing cartridge 110 and the handle and threaded cap 116 are put into place. A vacuum is created within the mixing container 104 by actuating an actuator 126 on the vacuum pump 102 and the user actuates handle 114 to mix the cement materials with mixing plate 118 to the proper viscosity.

Figure 2:
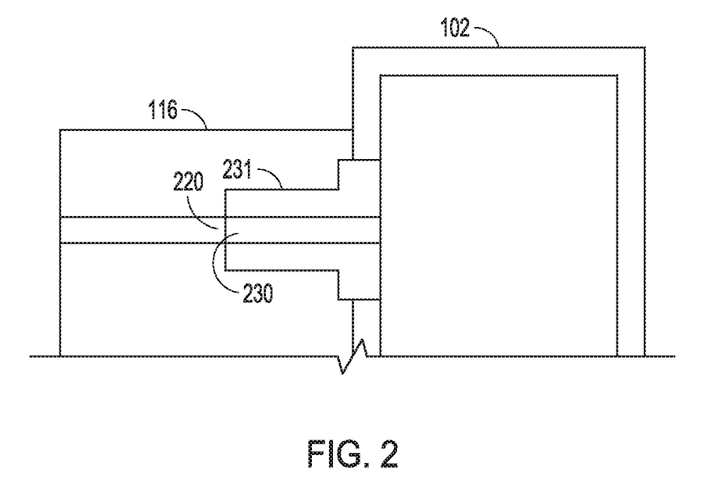
FIG. 2 shows a schematic cross section view of a connection between a vacuum pump and a cement mixing container, in accordance with one embodiment.

FIG. 2 shows a schematic representation of the connection between the vacuum pump 102 and the cement mixing container 104, in accordance with one embodiment. In this example, a port 220 at an exterior surface of the cap 116 directly engages a vacuum port 230 located at the exterior surface of the vacuum pump 102. This ease of connection between the vacuum source and the cement mixing container 104 provides that no hoses or external vacuum devices are needed. All that is needed to form a sufficient vacuum for mixing within cement mixing container 104 is provided by the vacuum pump 102 alone.

This design is helpful because if external vacuum pumps are used, the vacuum pumps are expensive and need to be cleaned after use. Moreover, vacuum hoses for connecting the vacuum pumps to the vacuum mixing systems are required. Prior to the mixing using such a vacuum mixing system, the vacuum pump first needs to be set-up and must be connected to an energy source, such as compressed air or electrical power. Then, the vacuum pump is connected to the vacuum mixing system by means of a vacuum hose. Said installation steps take up costly time and are potentially error-prone. The vacuum pump and connecting conduits to the vacuum mixing system and to external energy sources and supply conduits take up space and are potential tripping hazards and stumbling blocks. Moreover, the hoses may extend between sterile and non-sterile areas. Accordingly, the direct connection of the present design and self-contained vacuum source can help solve these issues.

Figure 3:
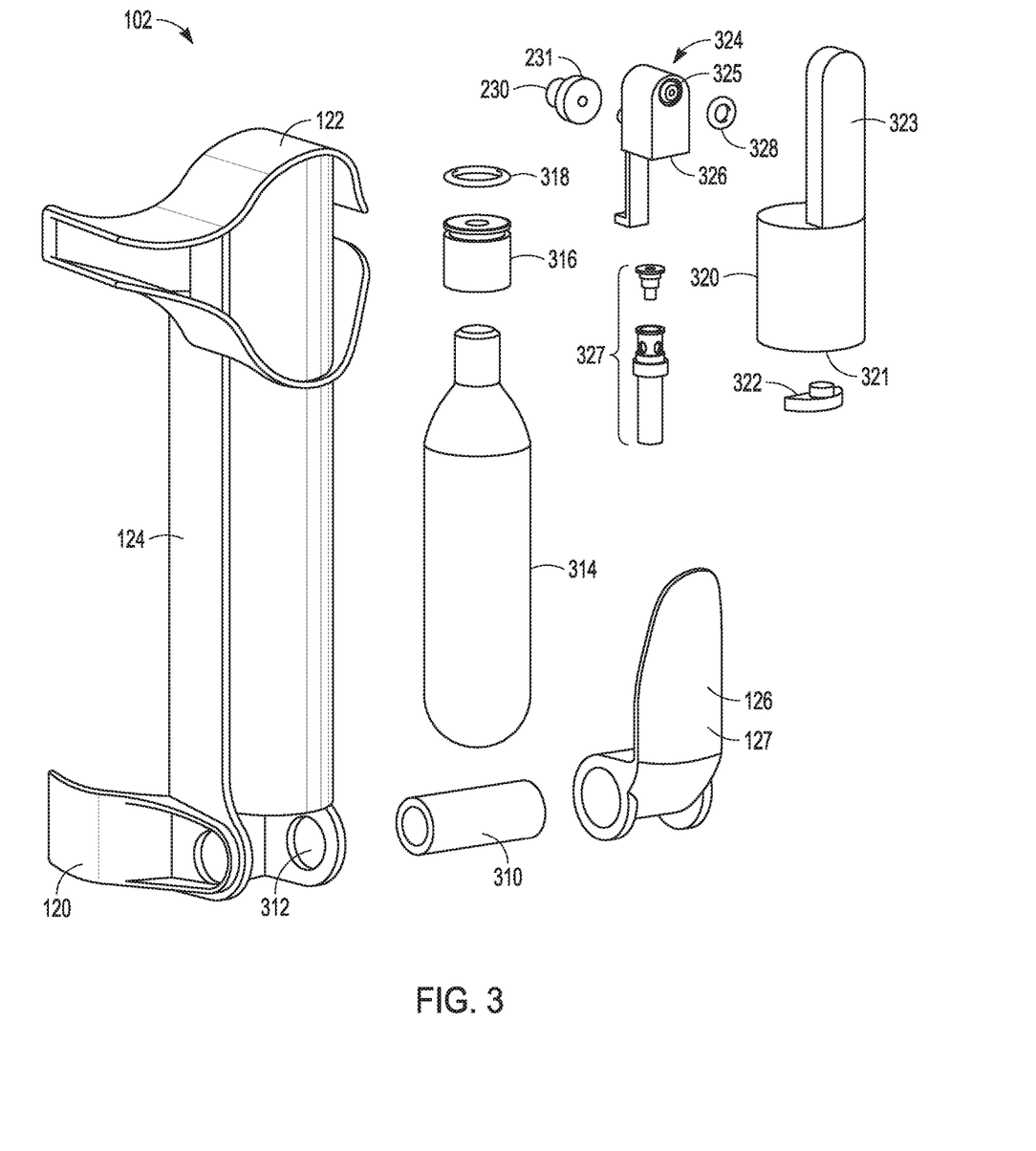
FIG. 3 shows an exploded isometric view of vacuum pump, in accordance with one embodiment.
Figure 4:
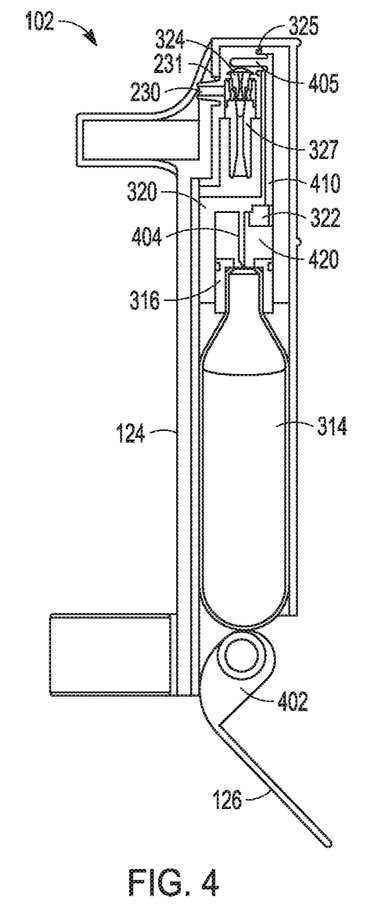
FIG. 4 shows a cross-section of the vacuum pump of FIG. 3, in accordance with one embodiment.
Figure 5:
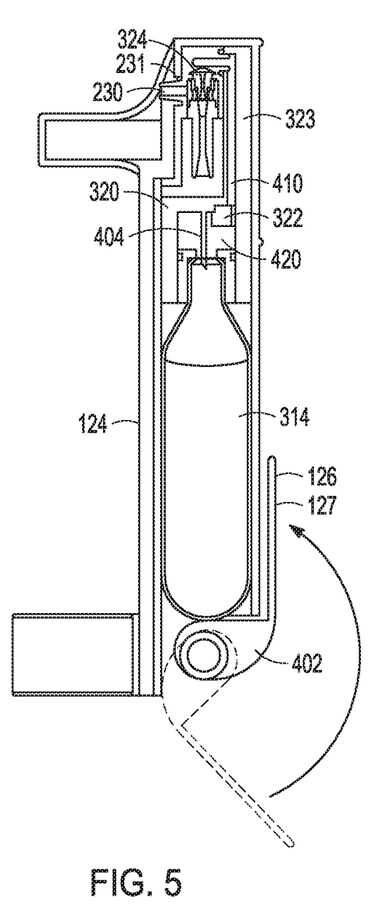
FIG. 5 shows another cross-section of h vacuum pump of FIG. 3, in accordance with one embodiment.
Figure 6:
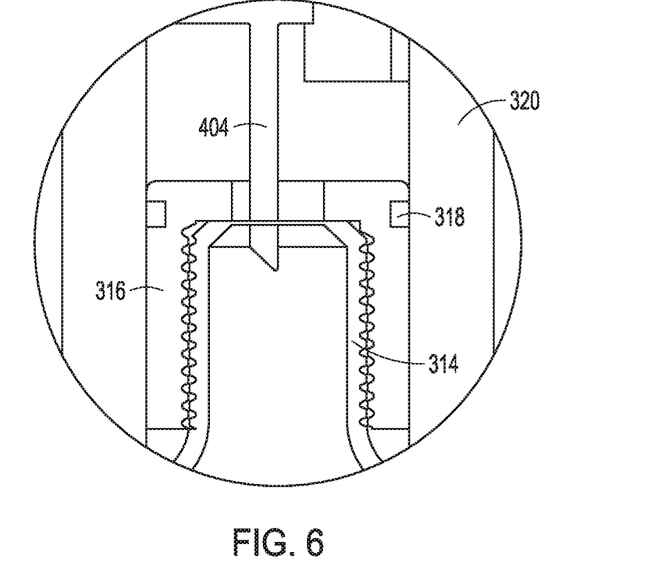
FIG. 6 shows a close-up view of a portion of FIG. 5.

FIG. 3 shows an exploded view of the components of vacuum pump 102, in accordance with one embodiment. FIGS. 4 and 5 shows a cross-section view of the vacuum pump 102 as assembled. FIG. 6 shows a close-up view of a portion of the vacuum pump 102 in operation.

In one embodiment, the vacuum pump 102 includes the pump body 124, and a gas container 314 located within the pump body by being inserted in an open bottom end of the pump body 124. In one example, the gas container 314 can contain $CO_2$. The vacuum pump 102 further includes the two or more arms 120, 122 arms extending from the pump body 124 configured to hold the cement mixing container (FIG. 1). In an example, the two or more arms 120, 122 can be curved so as conform to and grip the curved sides of the cement mixing container 104.

The vacuum port 230, which is the port of a non-return valve 231 is exposed on an exterior surface of the pump body 124 and positioned to engage the port 220 on the cement mixing container 104 (FIG. 2).

A venturi 324 is positioned adjacent the non-return valve 231 with the vacuum port 230 to create the vacuum at the vacuum port 230 when gas flows through the venturi 324. The non-return valve 231 conserves the vacuum within the cement mixing container 104 after the gas container 314 is empty. This design helps limit or eliminate user-error when using the system. The venturi 324 includes a main body 326 which holds the venturi tubes 327. An input port 325 on the body 326 receives gas from a perforator 320 to create a vacuum at vacuum port 230.

The perforator 320 is also located within the pump body 104 and is configured to puncture the gas container 314 to release gas to the venturi 324 to create a vacuum at the vacuum port 230. As noted above, with the present design the vacuum port 230 directly engages the port 220 on the cement mixing container 104 (FIG. 2) without intervening hoses.

Figure 7:
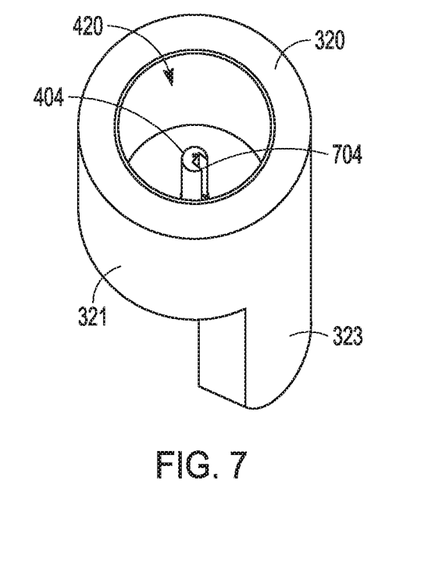
FIG. 7 shows an isometric view of a bottom of a perforator, in accordance with one embodiment.
Figure 8:
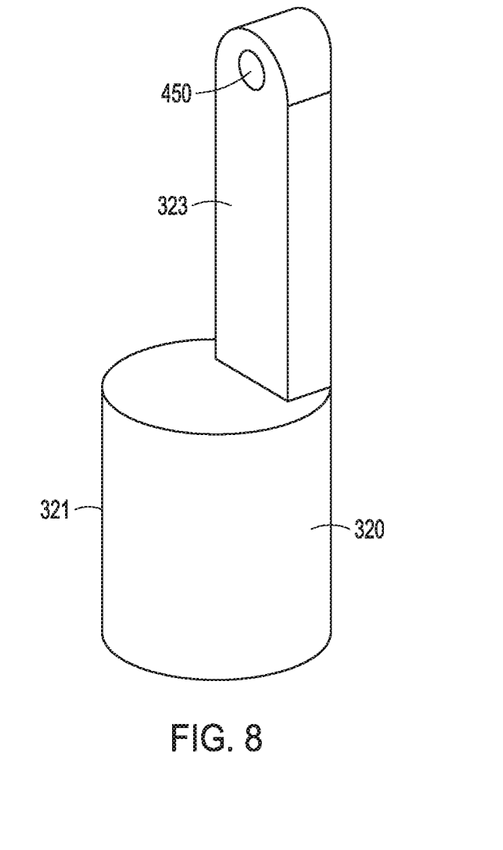
FIG. 8 shows an isometric view an upper portion of the perforator of FIG. 7, in accordance with one embodiment.

FIGS. 7 and 8 show further details of the perforator 320. FIG. 7 shows an isometric view of a bottom of the perforator 320 and FIG. 8 shows an isometric view an upper portion of the perforator 320, in accordance with one embodiment. In one example, the perforator 320 includes a body 321 having a cavity 420 on one end to receive a neck of the gas container 314 (FIG. 5). The perforator 320 can include a needle 404 located within and extending from a bottom surface of the cavity 420 to puncture the gas container 314. The perforator 320 can further include an arm 323 extending from the body 321 and having an internal passage 410 (FIGS. 4 and 5) extending up to a hole 450 proximate the top of the arm 323 so as to release gas out of the hole 450. The needle 404 includes a groove 704 longitudinally extending along the needle 404 to allow gas to flow into the cavity 420 from the gas container when the needle 404 punctures the gas container.

Referring again also to FIGS. 3-6, a regulator 322 can be inserted with the cavity 420 of the perforator 320 at the location of the start of the passage 410. The regulator 322 can control the amount of gas released through passage 410 to the venturi 324. An O-ring 328 can be located to seal the coupling between the hole 450 and the input hole 325 of the venturi 324.

The actuator 126 can include a lever 127 which is configured to puncture the gas container with the perforator 320. For example, the lever 127 can be rotatably coupled to the pump body 124 using a pin 310 which fits into holes 312 of the pump body 124. In an example, the lever 127 can include a cam 402 positioned such that when the lever 127 is rotated the cam 402 engages a bottom of the gas container 314 and pushes the gas container 314 up to the perforator 320 so as to puncture the gas container 314 with the needle 404. Accordingly, as shown in FIG. 5, when the lever 127 is rotated up to the pump body 124, the gas container 314 is pushed upward within the cavity 420 of perforator 320 until the needle 404 penetrates the closed top of the gas container 314. This releases the gas from the gas container 314 into the cavity 420 and then through the regulator 322, up the passage 410 and out to the venturi 324, where the gas flows through e venturi 324 forming a vacuum at vacuum port 230.

A seal member 316 is configured to receive a neck of the gas container 314. The seal member includes an external O-ring 318 to seal against an inner wall of the cavity 420 of the perforator 320.

Figure 9:
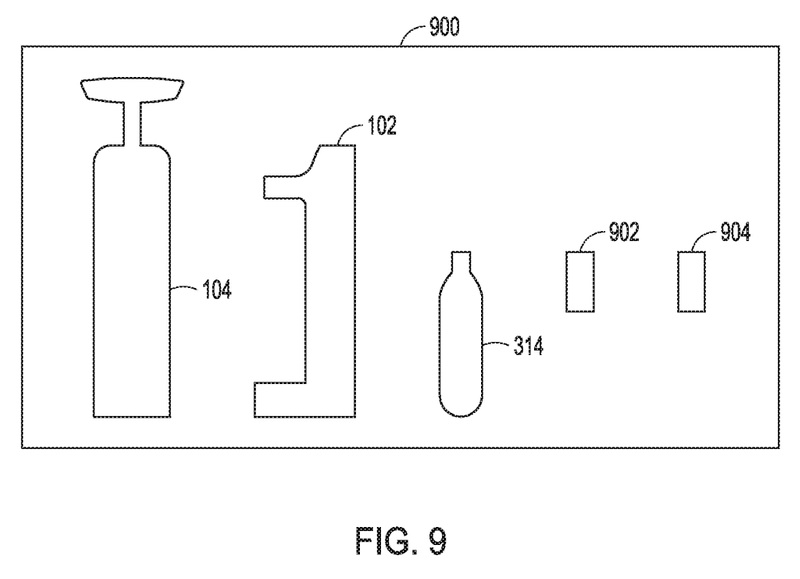
FIG. 9 shows a kit for making a cement mixture, in accordance with one embodiment.

FIG. 9 shows a kit 900 for making a cement mixture, in accordance with one embodiment. For example, the kit 900 can include a sterile container 901 holding the cement mixing container 104, the vacuum pump 102 and a gas container 314. The kit can further include one or more cement materials 902, 904 which will be mixed together. For example, the cements materials can include a liquid including a methyl-metacrylate and a powder including a polymethyl-metacrylate. The kit 900 can be supplied to users and includes everything to make a cement mixture without having the need to have an external vacuum source, power sources, or any hoses.

In some example, the system described herein can be a single use or multi-use system. For example, a new gas container can be placed with the vacuum pump 102 and the pump can be used multiple times. It can be simple to replace the gas container since it slips into the open bottom of the pump body 124.

In using the system described above, a user can attach the vacuum pump 102 directly to the cement mixing container 104 such that the port 220 on the cement mixing container 104 directly engages the vacuum port 230 on the vacuum pump 102. The user then actuates the vacuum pump 102 using lever 127 to release gas to the venturi 324 and create a suitable vacuum at the vacuum port 230. When a suitable vacuum is reached within the cement mixing container 104, the user mixes the cement mixture with the cement mixing container 104 by using the handle 114 and the mixing plate 118.

Due to the self-contained gas container for creating a vacuum, the lack of any connection hoses, the simple lever action control, and the non-return valve 230 conserving the vacuum, the present system present design provides simple operation while limiting any user-error.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

What is claimed is:

1. An apparatus comprising:
a pump body;
two or more arms extending from the pump body configured to hold a cement mixing container;
a vacuum port exposed on an exterior surface of the pump body and positioned to engage a port on the cement mixing container;
a venturi positioned proximate the vacuum port;
a perforator within the pump body, the perforator configured to puncture a gas container to release gas to the venturi to create a vacuum at the vacuum port; and
an actuator configured to puncture the gas container with the perforator.

2. The apparatus of claim 1, wherein the two or more arms are curved so as to grip the sides of the cement mixing container.

3. The apparatus of claim 1, wherein the vacuum port directly engages the port on the cement mixing container without intervening hoses.

4. The apparatus of claim 1, wherein the perforator includes a body having a cavity on one end to receive a neck of the gas container.

5. The apparatus of claim 4, wherein the perforator includes a needle located with the cavity to puncture the gas container, the perforator further including an arm extending from the body and having a passage so as to release gas out of a hole proximate the top of the arm.

6. The apparatus of claim 5, further including a regulator inserted with the cavity of the perforator.

7. The apparatus of claim 1, wherein the actuator includes a lever rotatably coupled to the pump body.

8. The apparatus of claim 7, wherein the lever includes a cam positioned such that when the lever is rotated the cam engages a bottom of the gas container and pushes the gas container up to the perforator.

9. The apparatus of claim 1, including a seal member to receive a neck of the gas container, the seal member including an external O-ring to seal against an inner wall of a cavity of the perforator.

10. A system comprising:
a cement mixing container;
a pump body;
a gas container located within the pump body;
two or more arms extending from the pump body configured to hold the cement mixing container;
a vacuum port exposed on an exterior surface of the pump body and positioned to engage a port on the cement mixing container;
a venturi positioned proximate the vacuum port;
a perforator within the pump body, the perforator configured to puncture the gas container to release gas to the venturi to create a vacuum at the vacuum port; and
an actuator configured to puncture the gas container with the perforator.

11. The apparatus of claim 10, wherein the vacuum port directly engages the port on the cement mixing container without intervening hoses.

12. The apparatus of claim 10, wherein the perforator includes a body having a cavity on one end to receive a neck of the gas container.

13. The apparatus of claim 12, wherein the perforator includes a needle located with the cavity to puncture the gas container, the perforator further including an arm extending from the body and having a passage so as to release gas out of a hole proximate the top of the arm.

14. The apparatus of claim 13, further including a regulator inserted with the cavity of the perforator.

15. The apparatus of claim 10, wherein the actuator includes a lever rotatably coupled to the pump body.

16. The apparatus of claim 15, wherein the lever includes a cam positioned such that when the lever is rotated the cam engages a bottom of the gas container and pushes the gas container up to the perforator.

17. The apparatus of claim 10, including a seal member to receive a neck of the gas container, the seal member including an external O-ring to seal against an inner wall of a cavity of the perforator.

18. A method comprising:
providing a vacuum pump including a pump body having two or more arms extending from the pump body configured to hold a cement mixing container;
attaching the vacuum pump directly to the cement mixing container such that a port on the cement mixing container directly engages a vacuum port exposed on an exterior surface of the pump body on the vacuum pump;
actuating the vacuum pump by using a perforator within the pump body, the perforator configured to puncture a gas container to release gas to a venturi positioned proximate the vacuum port to create a vacuum at the vacuum port; and
mixing a cement mixture with the cement mixing container.

19. The method of claim 18, wherein the vacuum pump includes a gas container and a venturi.

20. The method of claim 19, including a perforator within a pump body of the vacuum pump, the perforator configured to puncture the gas container to release gas to the venturi to create a vacuum at the vacuum port; and an actuator configured to puncture the gas container with the perforator.

* * * * *